United States Patent [19]
Cabrera et al.

[11] 4,387,076
[45] Jun. 7, 1983

[54] SAMPLE FEEDING ARRANGEMENT

[75] Inventors: Pedro P. Cabrera; Glenn D. Talbot, both of Miami; Larry C. Carman, Hialeah, all of Fla.

[73] Assignee: Coulter Electronics, Inc., Hialeah, Fla.

[21] Appl. No.: 311,221

[22] Filed: Oct. 14, 1981

[51] Int. Cl.³ ............................................. G01N 31/02
[52] U.S. Cl. ..................................... 422/67; 422/65; 422/66; 141/130
[58] Field of Search ............................. 422/65, 66, 67; 141/130

[56] References Cited
U.S. PATENT DOCUMENTS

| | | | |
|---|---|---|---|
| 3,504,376 | 3/1970 | Bednar et al. | 422/67 X |
| 3,624,223 | 11/1971 | Smythe | 422/66 X |
| 3,762,879 | 10/1973 | Moran | 422/65 X |
| 4,311,484 | 1/1982 | Fosslien | 422/65 X |

*Primary Examiner*—Robert L. Lindsay, Jr.
*Attorney, Agent, or Firm*—Gerald R. Hibnick

[57] ABSTRACT

A sample feeding arrangement which receives sealed sample tubes, moves them one at at time to a seal piercing and sample aspiration station, and then discharges the used tubes. This sample feeding arrangement is mounted inside a sample analyzer of the type which previously had operated semiautomatically. Receipt of a sample tube at the infeed station of this feeding arrangement initiates the repositioning of the tube to an aspiration station, which thereat enables all other handling steps of the tube, sample aspiration, and the full system cycle of the analyzer.

10 Claims, 3 Drawing Figures

SAMPLE FEEDING ARRANGEMENT

BACKGROUND OF THE INVENTION

This invention concerns a feeding arrangement for samples carried in closed containers having a pierceable portion through which sample can be removed, as by a hollow needle. More specifically, this invention concerns an automatic arrangement for carrying closed sample containing tubes into an automated sample testing apparatus, removing sample from the closed tubes sequentially, supplying sample into the testing apparatus, ejecting the used tubes, and cleaning the sample removing and supplying portions between each supply step.

The just described functions are, in fact, known per se, as evidenced, for example, by apparatuses discloses in the following U.S. Pat. Nos. 3,418,080; 3,607,097; 3,768,526; 3,883,305; and 4,120,662. General problems with such prior art examples are that they are mechanically and fluidically cumbersome, expensive and not easily adaptable to the needs of many laboratories, where compactness of equipment and close proximity of human operator to instrument is desired. Because of the high cost of testing samples in hospitals and laboratories, economy and simplicity of instrumentation are now becoming the requirements, even more so than highest precision.

Some well known and accepted testing instruments heretofore have not had automatic sample feeding capabilities for reasons including the just named prior art deficiencies. One such instrument is the Coulter Counter ® Model S multiparameter blood analyzer. (Coulter Counter is the Registered Trademark No. 679,591 of Coulter Electronics, Inc., Hialeah, Florida.) The system operations of such analyzer are disclosed in U.S. Pat. No. 3,549,994. If such an analyzer could receive sample tubes directly from the phlebotomist without any prediluting, or transferring to another vessel, or even opening of the tube, an act which could expose the operator and laboratory to disease, such as hepatitis, and then aspirate an aliquot of the sample from the closed tube for activating normal analyzer testing, all in a compact and inexpensive manner, then a technologic advance would be achieved.

SUMMARY OF THE INVENTION

A sample tube receiving cradle is mounted to the sample analyzer, close to its mixing and diluting valve. The cradle receives one sealed sample tube at a time from the human operator, or an infeed arrangement, but handles three tubes in different stages of processing: receipt of tube, activation of analyzer system and sample transfer from tube into the system, and ejection of used tube. After sample transfer, the sample aspiration needle and associated fluid lines are cleaned to avoid intersample contamination and carryover. Cleaning of the needle tip is in a rinse bath, through which the tip reciprocates, on its way to the sealing stopper of the sample tube.

DETAILED DESCRIPTION OF THE PREFERRED EMBODIMENT

Figure 1:
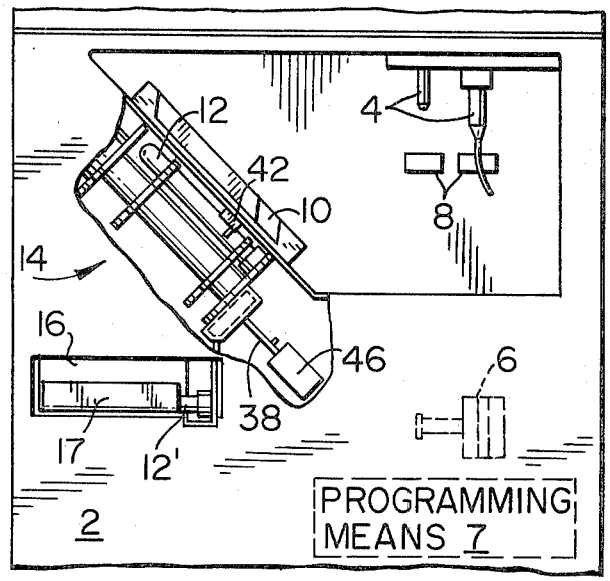
FIG. 1 is a fragmentary view, broken away, of the front of a sample analyzer containing the sample feeding arrangement of this invention.

With reference to FIG. 1, which shows a portion of the front of a sample analyzer 2, such as a Coulter Counter ® Model S blood analyzer, there typically would be one or more aspirator probes 4 which would suck up blood from an open container holding either a whole blood sample or a prediluted blood sample. The open container, not shown, would be brought to the probe tip by the hand of a human operator, who would have received a sealed tube of patient blood from the phlebotomist. The operator would ensure that the sealed tube with its patient sample had been mixed, either manually or by a device such as a Coulter ® Bloodmixer (Coulter is the Registered Trademark No. 995,825 of Coulter Electronics, Inc.). Thereupon, the operator would open the tube and present it to the aspirator probe 4, or, if the sample was of very small volume, such as from an infant, the operator would predilute the sample into another open container and then present that container to the aspirator probe. The handling of blood in open containers is not desirable since disease, such as hepatitis, can thereby be transmitted. Of course, if the time required for operator handling could be reduced, a cost savings would be effected. Although blood samples and a blood analyzer are detailed herein, the analyzer could be for other sample substances, as in chemistry, pollution control, etc.

Coupled to the aspirator probes, by fluid lines not shown, is a sample diluting and transfer valve 6, the construction and operation of which can be as disclosed in U.S. Pat. Nos. 3,549,994 or 4,152,391 and now is well known in the hematology analyzer field. Control over the operation of the transfer valve and most other functions of the analyzer is by internal automated programming means 7 as is taught, for example, in U.S. Pat. No. 3,549,994 and same is not impeded by the operation of this new sample feeding arrangement; however, as next will be explained, the sample feeding arrangement adds further automated features and triggers the system cycle through the programming means 7. In prior art analyzers, such as the Model S, when the operator presents the open sample container to the system at the probe 4, the operator next must activate the aspiration by a manual control lever or button 8 on the front of the system. Thereupon, the system programming means 7 takes over control and advances the processing throughout the full system cycle. According to the present invention, the sealed sample tube itself, upon receipt by the sample feeding arrangement, not only will initiate sample transfer, but also initiate the entire and progressive system cycle programming means 7. Hence, the probes 4 and control button need not be used and need not even be part of the system.

Figure 2:
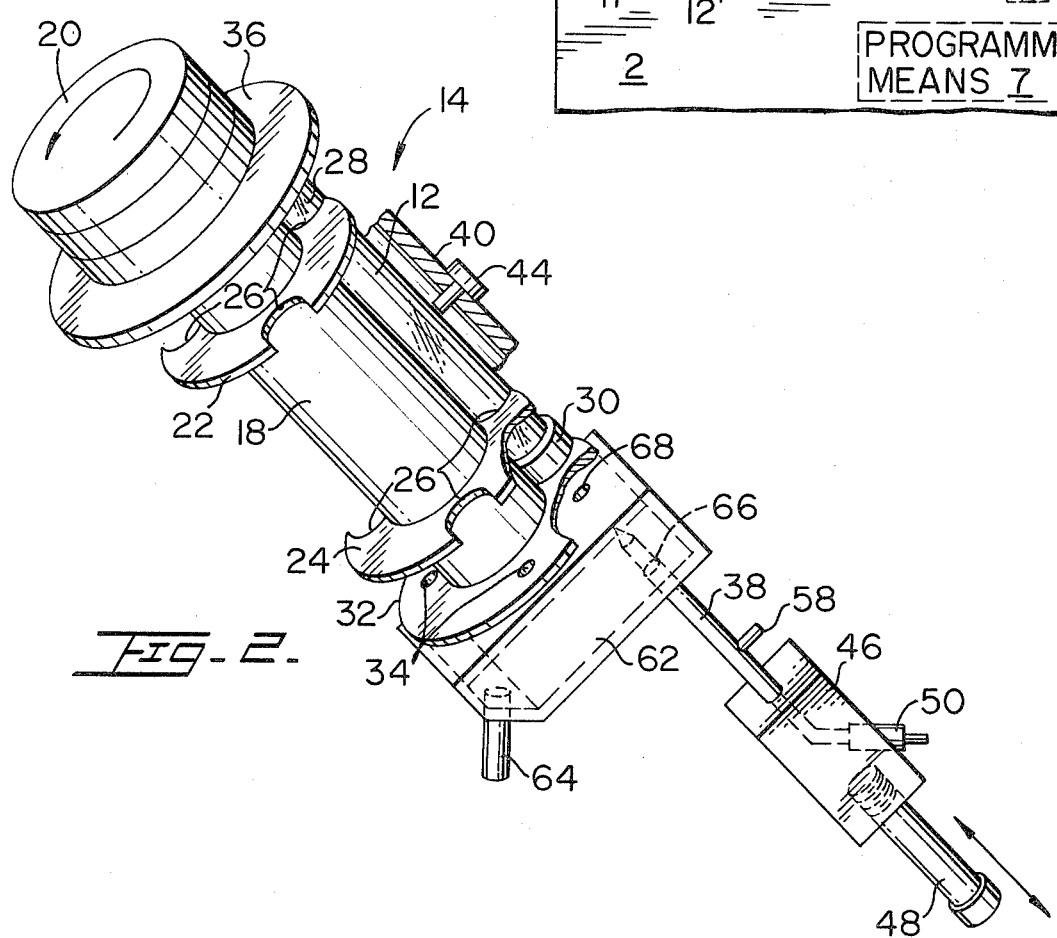
FIG. 2 is a perspective view, partly diagrammatic, of the major components of the invention.

The front of the analyzer is provided with a small entry window and guideway or receiving station 10, shaped to the contours of a sample tube or container 12 so as to guide the placement of the sample tube into a cradle 14, which is better viewed in FIG. 2. An input feed tray, not illustrated, can be provided and positioned to open into the guideway 10, for holding a few of the sample tubes 12 and advancing them, one at a time, in the guideway. A used tube discharge port 16 also is provided on the front of the analyzer, for receiving used tubes 12' as they are ejected from the cradle, as will be detailed subsequently. The port 16 can be fitted with a collection tray or the like 17, which would hold a plurality of the used tubes 12' for ease of disposal.

For ease in illustration and viewing, FIG. 2 is rotated approximately 120° from the position shown in FIG. 1. As shown in FIG. 2, the cradle 14 has a spindle 18 which is rotatable by a motor 20, or other drive means. Brackets and other mounting and joining hardware are not illustrated, so as to simplify the drawing for ease of viewing. The illustrated cradle is designed to handle three tubes displaced 120° from each other; however, more tubes and other angular displacements could be provided if desired. A pair of similarly notched discs 22 and 24 serve to position the tubes relative to the spindle and each other and have semicircular notches 26 into which the tubes will seat. The longitudinal spacing between the discs 22 and 24 is less than the length of a tube 12, so that the bottom end 28 of the tube will rise above the upper disc 22, and the stopper-sealed opening will be below the lower disc 24 and thereby the face of the stopper 30 will be accessible.

A base plate 32 is at the lower end of the spindle and rotates therewith. In the base plate and axially aligned with the notches 26 are three pass-through orifices 34, (only two of which are shown, the third being in the broken away portion underlying the stopper). Thus aligned, the center of the face of the stopper 30 will be directly above an orifice 34, for reasons to be described. At the upper end of the spindle is a cover member 36, which could be secured to the spindle or be a fixed member, such as part of the mounting bracket for the cradle. The lower surface of the cover member could be provided with cushion means to protect the closed end of the tube 12 during aspiration, at which time the tube is pushed slightly upward by action of the aspiration needle 38.

The FIG. 1 view has the sample tube 12 positioned as if it has just been inserted into the cradle. In FIG. 2, the view is after the cradle has been advanced its first 120° step, so that the tube now is aligned with the needle 38 and also the pass-through orifice 34 which underlies the stopper 30. Also as shown, the cradle lies at an angle of approximately 45° with respect to vertical, so that gravity will cause the liquid sample to be at the stopper end of the tube. Hence, when the needle punctures the stopper, it will not encounter air at the interior side of the stopper.

After the sample aliquot has been drawn from the tube 12 and the needle 38 has withdrawn from the stopper and the orifice 34 to a position below the base plate 32, the motor 20 will be activated to again step the cradle 120° to place the used tube into the discharge position, at which gravity will cause the tube to drop free from the notches 26 and fall to the level of the discharge port 16 and be received by the tray 17. To prevent a sample tube from moving outward of the notches after loading and prior to reaching the discharge position, there can be provided a curved retainer member 40 which closely overlies the cradle for approximately 180°, terminating at the discharge position. Only a fragment of the retainer 40 is illustrated, for ease of viewing. The retainer can be a portion of the cradle bracket mounting means.

A sensing element 42, such as a microswitch, is located to be activated by the presence of a sample tube 12 as it enters the window 10 and seats into the cradle 14 as is positioned in FIG. 1. Such switch can be mounted to the inside of the front of the instrument, as shown in FIG. 1. When activated, this switch 42 will engage the motor 20 to rotate the cradle approximately 120° and align the sample tube with the aspiration needle 38, as shown in FIG. 2. When the sample tube achieves the desired alignment, a second sensor element, such as a microswitch 44, is engaged and it initiates the full system cycle of the entire analyzer, including the sample feeder.

Preferably, it is the tube itself and not another object which engages the switch 44. The making of the switch 44 activates the system programming means, which thereupon carries out all other system control—both analyzer and feeder.

Figure 3:
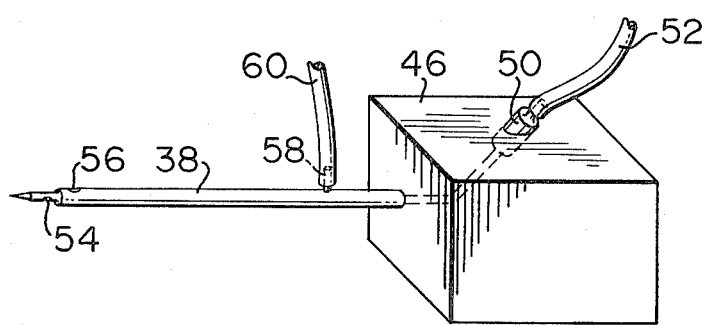
FIG. 3 is a perspective view of the transfer needle and its housing.

The aspiration needle 38 is secured into a needle housing 46. The housing is secured to a drive means 48, such as a solenoid or air piston, for reciprocating the needle into and out from the tube 12, through the stopper 30. The housing 46 has a fluid line connector 50 to which is coupled a fluid line 52 (shown in FIG. 3) leading to the diluting and transfer valve 6. The needle 38 is coaxial, with its central bore forming a passageway feeding into the fluid line 52. The entry into the central bore is at a port 54 near, but not quite at, the needle tip. The port 54 is spaced from the tip so that the port does not become plugged by any piece of the stopper 30 which might break loose during penetration. The second fluid path within the coaxial needle is for venting the sealed tube to atmosphere during aspiration of the sample. As well known, contents of a sealed container cannot be withdrawn unless there is displacement by a substance, such as air, into the container. A vent port 56 and a vent line connector 58 are at the ends of the vent passageway and couple to a vent line 60.

A rinse bath 62 is interposed in the path of the needle tip and is fixedly mounted. The bath forms a closed chamber, except for a drain 64, and needle entry and exit bores 66 and 68. The bores are aligned with the pass-through orifice 34 of the base plate 32 for the aspiration position, as shown in FIG. 2. The size and orientation of the bath 62 are such that, in the normally retracted position of the needle 38 as shown in FIG. 2, the needle tip, the sample entry port 54 and the vent port 56 all lie within the bath. When in this retracted position, for a portion of the total system cycle, the fluid line 52 and the vent line 60 are coupled to sources of rinse fluid, which fluid is fed through both paths of the coaxial needle and into the bath chamber via the ports 54 and 56. Rinse fluid flowing from the vent port 56 will clean the outside of the needle tip. After liquid rinsing, the vent line is coupled to a source of clean air or gas and blown clean and dry. The fluid line 52 and the central bore of the needle is to remain filled with the rinse liquid until the next aliquot is drawn, thereby avoiding the problem of trapped air in the aspirating system.

The sequencing of the sample feeding arrangement has, for the most part, been described hereinabove, but next will be summarized. A sample tube 12 is placed through the entry window 10 and trips the switch 42 to activate the motor 20 to advance the cradle 14 so that the tube is in the aspirating position shown in FIG. 2. Thereupon, the switch 44 initiates the system cycle, via the programming means 7, the first portion of which causes the drive means 48 to advance the needle 38 and its housing 46 upward, such that the needle tip is moved from within the rinse bath 62 to within the sample tube 12, of course through the stopper 30. At this juncture, the well known analyzer system operations commence without any manual interaction. First, sample aspiration is accomplished, with sample being drawn through the needle and the fluid line 52 into the diluting and transfer valve 6. Aspiration into the valve and further system operations can be as taught in U.S. Pat. No. 3,549,994.

At times convenient to the system cycle, the drive means 48 returns the needle tip to the rinse bath 62, where the previously described fluid wash, air clean-dry and clean rinse fill steps are accomplished, with the feeder motor stepping ahead 120° to cause the just used sample tube to be dropped into the discharge port 16 and tray 17. If a new sample tube trips the switch 42 early during the sequencing of the system steps, its command to the motor 20 is acknowledges but not utilized until later in the system cycle, when the system next can accept a new sample.

It is believed that the disclosed embodiment will enable those skilled in the art to practice the invention and that variations and substitutions of equivalents are capable of being made without departing from the spirit and scope of the invention as defined in the appended claims.

What we claim is:

1. A sample feeding arrangement for operatively introducing a sealed sample container into a semiautomatic sample analyzer for thereupon enabling the analyzer automatically to obtain sample material and automatically to sequence through a full analyzer cycle, said feeding arrangement comprising: sample container holding means for receiving a sealed sample container and for positioning same into a sample drawing position, control means responsive to the sample container being properly positioned for sample drawing, said container holding means being coupled to sample drawing means for withdrawing sample from the sealed container, and said control means being operatively coupled to analyzer system programming means for automatically enabling said sample drawing means and other of the analyzer operations.

2. A sample feeding arrangement according to claim 1 in which said sample container holding means is constructed to hold at least two sample containers in different positions, one said position being aligned with a container receiving station of said feeding arrangement and another said position being aligned with said sample drawing means.

3. A sample feeding arrangement according to claim 2 which further comprises motive means for said sample container holding means for transporting a sample container from said one position to said another position, said motive means being enabled by a container when it is at said one position.

4. A sample feeding arrangement according to claim 3 in which said container holding means has a longitudinal axis of rotation, said containers are retained parallel to said axis, and said axis is remote from being horizontal such that sample material is oriented at the sealed end of the container and proximate to said sample drawing means.

5. A sample feeding arrangement according to claim 4 in which the construction of said container holding means and the orientation of said axis of rotation, relative to said another position, is such that rotation of said container holding means beyond said another position, after sample drawing, subjects the container to sufficient gravitational force to free the container from the container holding means.

6. A sample feeding arrangement according to claim 1 in which said sample container is sealed at one end by a piercable stopper, said sample drawing means includes an aspiration needle reciprocable in a path through said stopper, and said container holding means holds said container such that the stopper is below the sample and above said needle.

7. A sample feeding arrangement according to claim 6 in which aspiration needle rinsing means is interposed into said path.

8. A sample feeding arrangement according to claim 7 in which both said rinsing means and said container holding means include alignment means for said aspiration needle along said path.

9. A sample feeding arrangement according to claim 1 in which the sample drawing means includes an aspiration needle having: a container seal piercing point, a first port and a second port both near, but spaced sufficiently from said piercing point so as not to be plugged by debris from the container seal, said needle defining two separate passageways, each communicating with only one of said ports and each terminating at separate exits which are remote from said piercing point; whereby, one passageway can be coupled to aspirate the sample from the container while the other passageway is coupled to carry gas into the container for venting same.

10. A sample feeding arrangement according to claim 9 in which said exits can be coupled to cleaning material to be fed through said passageways and out from said ports, and at least one of said ports is positioned such that the cleaning material also will clean the exterior of said needle tip.

* * * * *